United States Patent [19]

Dobkin

[11] Patent Number: 4,717,564
[45] Date of Patent: Jan. 5, 1988

[54] HIGH TITER VARICELLA-ZOSTER IMMUNE GLOBULIN FOR INTRAVENOUS ADMINISTRATION

[75] Inventor: Milton B. Dobkin, Lafayette, Calif.

[73] Assignee: Miles Laboratories, Inc., Elkhart, Ind.

[21] Appl. No.: 23,734

[22] Filed: Mar. 9, 1987

Related U.S. Application Data

[62] Division of Ser. No. 795,811, Nov. 7, 1985, Pat. No. 4,665,159.

[51] Int. Cl.$^4$ .............................................. A61K 39/25
[52] U.S. Cl. ..................................... 424/86; 424/85; 424/89; 424/101; 530/387; 530/388; 530/389; 530/390; 530/391; 530/830
[58] Field of Search ............................ 424/85, 86, 89; 530/387, 388, 389, 390, 391, 830

[56] References Cited

U.S. PATENT DOCUMENTS

| | | | |
|---|---|---|---|
| 3,903,262 | 9/1975 | Pappenhagen | 530/387 |
| 4,174,388 | 11/1979 | McAleer | 424/86 |
| 4,186,192 | 1/1980 | Lundblad | 514/21 X |
| 4,296,024 | 10/1981 | McAleer | 530/387 |
| 4,396,608 | 8/1983 | Tenold | 424/85 X |
| 4,499,073 | 2/1985 | Tenold | 424/85 |
| 4,617,379 | 10/1986 | Dobkin | 424/85 X |
| 4,665,159 | 5/1987 | Dobkin | 530/387 |

OTHER PUBLICATIONS

Zaia, J. Int. Dis. 137, No. 5, 601–604, (1978).
Amer., J. Med., 124–127, Mar. 1984, Paryani.
J. Pediatrics, 105(2), 200–205, (1984), Paryani, published Aug. 1984.
J. Amer–Med., ASSN–251, (11), 1401, 1405, 1409, 1413, (1984), Immunization Practices Advisory Commission.

Primary Examiner—Howard E. Schain
Attorney, Agent, or Firm—James A. Giblin

[57] ABSTRACT

Normal plasma from donors who have not been vaccinated with a varicella-zoster vaccine can be screened for higher than normal titers of naturally occurring antibody to varicella-zoster virus. Those plasmas with high titers of such antibody can be pooled and fractionated to give hyperimmune globulin. The product may be treated to render it suitable for intravenous injection. Patients with varicella-zoster infection or at risk to such infection, may receive the present product to raise serum titers of varicella-zoster antibody.

6 Claims, No Drawings

HIGH TITER VARICELLA-ZOSTER IMMUNE GLOBULIN FOR INTRAVENOUS ADMINISTRATION

This application is a division of application Ser. No. 795,811, filed Nov. 7, 1985, now U.S. Pat. No. 4,665,159.

BACKGROUND OF THE INVENTION

1. Field of the Invention

This invention relates to and has among its objects a novel immune globulin and novel methods for its production. Particularly, the invention is concerned with an intravenously injectable immune globulin having a high titer of naturally occurring antibody to varicella-zoster virus (VZV). Further objects of the invention will be evident from the following description wherein parts and percentages are by weight unless otherwise specified.

2. Description of the Prior Art

Hyperimmune serum globulins, i.e., immune serum globulins having high titers of a particular antibody, are therapeutically useful in treating patients deficient or in need of that particular antibody. For example, tetanus hyperimmune globulin is useful in treating tetanus, and rabies hyperimmune globulin, rabies. It is well known that hyperimmune globulins can be produced from plasma or serum obtained from selected donors who have significantly higher titers for a specific antibody than is normally found in the average population. These donors have either been recently immunized with a particular vaccine (U.S. Pat. No. 4,174,388) or else they have recently recovered from an infection or disease [Stiehm, *Pediatrics,* Vol. 63, No. 1, 301-319 (1979)].

Although clinical disease from VZV is not common among the general population, it is encountered very frequently in certain susceptible groups of patients. Immunosuppressed organ transplant and cancer patients have been identified as having an usually high risk of acquiring severe, and frequently fatal, VZV infection.

Zaia et al in *The Journal of Infectious Diseases,* Vol. 137, No. 5, 601-604 (1978) disclosed a practical method for preparation of VZV immune globulin for intramuscular administration. Outdated blood was screened for complement-fixing antibody to VZV. About 15% of the plasma units had a complement-fixation titer equal to or greater than 1:16, with about 7.5% greater than or equal to 1:32.

A report published in *Morbidity and Mortality Weekly Report,* Vol. 33 (No. 7), 84-100 (Feb. 24, 1984) [see also, *J. Amer. Med. Assn.,* 251 (11), 1401 (1984)] discloses a statement by the Immunization Practices Advisory Committee on the use of a varicella-zoster immune globulin (VZIG) product. This commercially available VZIG product is intended to be administered intramuscularly and should never by administered intravenously. See *Morbidity and Mortality Weekly Report,* 33 (7), 84-100 at page 96 (1984). See also *J. Amer. Med. Assn.,* 251 (11), 1401 at page 1413 (1984).

S. G. Paryani et al, *J. Pediatrics,* 105 (2), 200-205 (1984) and *Amer. J. Med.,* 124-127 (Mar. 30, 1984) disclose the results of a study which showed that administration of a modified immune serum globulin product that can be given intravenously (Gamimune®, Cutter Biological—Miles Laboratories, Inc., Berkeley, CA) to patients brought about a titer of antibody to VZV comparable to that brought about by intramuscular administration of VZIG. Table I in *J. Pediatrics,* 105 (2), 200 at 201 (1984) illustrates the comparison of VZV antibody titers of VZIG and IGIV lots used in the study wherein the titers were determined by three methods, namely, radioimmunoassay (RIA), enzyme-linked immunosorbent assay (ELISA) and indirect fluorescent antibody assay (IFA). This table shows that the ELISA VZV antibody titer of VZIG ($1:1.7 \times 10^6$) is about 18-fold that of IGIV (1:97,000).

Still, however, there is a need for a VZV immune globulin product having a higher than normal titer of antibody to VZV that may be administered intravenously.

SUMMARY OF THE INVENTION

I have found that normal fresh plasma from normal donors who have not been vaccinated with a VZV vaccine can be screened for higher than normal titers of antibody to VZV. Those plasmas with antibody titers greater than about 1:150,000, determined by means of an enzyme-linked immunosorbent assay (ELISA), can be pooled and then fractionated to give a VZV hyperimmune globulin or, more specifically, a high titer varicella-zoster immune globulin, that may be administered intravenously. This result is surprising because it is unexpected that plasma from normal, unvaccinated donors would have a titer of antibody to VZV high enough to yield a VZV hyperimmune globulin which would be effective in treating VZV infections by intravenous administration.

One obvious advantage of the invention is that normal donors need not be given a VZV vaccine. Consequently, the risks inherent in such a practice are avoided. Another advantage of the invention is that the hyperimmune globulin given intravenously makes antibodies to VZV immediately available. Another advantage resides in avoiding patient discomfort associated with intramuscular administration. Other advantages are elimination of a delay of several days for VZV antibodies to reach a peak in the circulation, and elimination of local degradation. Furthermore, less product needs to be administered intravenously in order to achieve the same level of antibody obtained with an intramuscularly administered product or higher doses can be administered intravenously to provide higher titers which would otherwise be difficult to obtain by intramuscular administration.

DESCRIPTION OF THE PREFERRED EMBODIMENTS

These and other advantages of the present invention may be obtained in the following manner.

Normal plasma from a donor is tested for naturally occurring antibody to VZV employing an ELISA or other equally sensitive screening method at equivalent titer. To be effective the plasma from such donors should have a titer of antibody to VZV equal to or greater than about 1:150,000. We have found that about 3-8% of plasma donors in fact have such a titer. These donations may be selected from a routine donor collection by random screening. Generally, the hyperimmune globulin of the invention has a titer of antibody to VZV of about 1:750,000-1:1,500,000, preferably about 1:800,000-1:1,350,000.

The method of screening the plasma, i.e., the ELISA method, is essentially as described by Engvall and Perlmann, *J. Immunol.,* 109, 129-135 (1972), Engvall et al,

*Biochemica Et Biophysica Acta,* 251 (1971) 427–434, Engvall et al, *Immunochemistry,* 8, 871–874 (1971), which are all incorporated herein by reference. The assay is a simple method for the quantitative determination of antibodies. Microtiter plates coated with antigen are incubated with antiserum followed by an enzyme-labeled preparation of anti-globulin. The enzyme-labeled anti-globulin remaining in the wells after washing and quantitated by addition of a chromogenic substrate, provides a measure of the amount of specific antibodies in serum.

Plasma having a sufficiently high titer of antibody is pooled and fractionated to obtain an immune globulin having a high titer of antibody to VZV. To this end one may employ any method for obtaining an intravenously injectable immune globulin from pooled plasma. For example, one may employ the Cohn fractionation method (referenced hereinbelow, which references are incorporated herein by reference thereto) an ammonium sulphate fractionation, polyethylene glycol precipitation or the like. The aforementioned immune globulin comprises IgG, usually at least 90% IgG monomer. The material generally also contains other globulins such as IgA, IgM, and the like.

These high titer plasmas are pooled and subjected to the Cohn fractionation method to produce Fraction II [Cohn et al, *J. Am. Chem. Soc.,* 68, 459 (1946) and Oncley, et al, ibid., 71, 541 (1949)].

The so-obtained hyperimmune globulin may be rendered intravenously injectable by treatment according to the method of Tenold, "Intravenously Injectable Immune Serum Globulin", U.S. Pat. Nos. 4,396,608 and 4,489,073, or of Pappenhagen et al, "Pharmaceutical Compositions Comprising Intravenously Injectable Modified Serum Globulins, Its Production and Use", U.S. Pat. No. 3,903,262 (which are incorporated herein by reference) or any of the methods referred to in the above-identified U.S. patents. The method according to U.S. Pat. No. 3,903,262, broadly, involves modification of the immune globulin by reduction and alkylation to render it intravenously injectable. The method according to U.S. Pat. Nos. 4,396,608 and 4,499,073 involves adjusting the pH and ionic strength of a solution of the immune globulin to render it intravenously injectable.

The hyperimmune globulin preparation of this invention can also include maltose as a stabilizer in accordance with the teaching of U.S. Pat. No. 4,186,192. Accordingly, the instant preparation may contain about 1–20% of maltose on a weight to volume basis.

The hyperimmune products of the invention may be manufactured as pharmaceutical preparations, usually aqueous solutions of the hyperimmune globulin which may be used for prophylactic and therapeutic purposes. The products are sterilized by any suitable means, usually by sterile filtration through appropriate conventional media, in the manufacture of the pharmaceutical preparations.

The pharmaceutical preparation intended for therapeutic use should allow delivery of a therapeutic amount of hyperimmune globulin, i.e., that amount necessary for preventive or curative health measures in the treatment of infection by varicella-zoster virus.

The invention is demonstrated further by the following illustrative examples.

Assay Method

The ELISA method was essentially the same as that described by Engvall and Perlmann, ibid., and used by Carlsson et al, *Inf. Imm.,* 6 (5) 703–708 (1972) for titration of anti Salmonella immunoglobulins. The method has been previously adapted for microtiter plates Voller et al, *Manual of Clinical Immunology,* 1976, 506–512, where visual endpoints can be determined with good sensitivity Poxton, *J. Clin. Path.,* 32, 294–295 (1975), Voller et al, supra. Round bottomed wells in polystyrene microtiter plates were sensitized by addition of 0.1 ml of the optimal dilution of VZV antigen in carbonate-bicarbonate buffer, pH 9.5, and incubated at 4° C. for approximately 18 hours. VZV antigen is obtained by infecting human cells with VZV and harvesting the viral antigen according to the procedure described by Forghani et al, "Antibody Assays for Varicella-Zoster Virus:Comparison of Enzyme Neutralization, Immune Adherence, Hemagglutination, and Complement Fixation", in J. Clin. Microbiol. 8:5, 545–552 (1978). Plates were washed once with phosphate buffered saline (PBS) containing 0.05% Tween 20 and 0.02% sodium azide (PBSTA). Five percent Bovine serum albumin (BSA), 0.1 ml was added to each well. The plates were further incubated 4–5 hours at room temperature, followed by one wash. The plates were shaken dry after the final wash. Dilutions of antisera were added to each well (0.1 ml) and incubated overnight at room temperature. Wells were washed three times as before and 0.1 ml of goat anti-human IgG conjugated to alkaline phosphatase (Miles Laboratories, Inc.) was added to each well and incubated 2 hours at room temperature. After again washing the wells, 0.1 ml of a 1.0% (w/v) solution of enzyme substrate, p-nitrophenyl phosphate, (Sigma Chemical Co.) in 10% diethanolamine buffer, pH 8.0, with 0.02% sodium azide and 1 mM $MgCl_2$ was added and incubated for 30 minutes, at room temperature. The reaction was stopped by the addition of 0.05 ml of 3N NaOH to each well. The absorbance was read at 405 nm with a Dynatech model 580 micro ELISA reader. The endpoint was taken to be the highest dilution with an absorbance $\geq 0.010$.

EXAMPLE 1

Plasma donations obtained from donors were screened for high titer of antibody to VZV using the ELISA method. Plasma donations with a VZV antibody titer less than 1:150,000 were pooled ("unselected") and those of 1:150,000 or greater were pooled ("selected"). The "selected" plasma pool, having an ELISA titer of 1:173,346, was fractionated to give an intravenously injectable VZV immune globulin. Also, the several "unselected" plasma pools were fractionated to give an intravenously injectable immune globulin.

Eleven normal (unselected) plasma pools were titrated for VZV antibody by ELISA the results obtained, set forth in Table 1, show that the antibody levels varied between 1:21,750 and 1:45,201 with a mean titer of 1:28,833. A comparison of the mean titer obtained with normal plasma pools and that found with the selected, high-titer plasma pool (1:173,346) set forth in Table 2 confirms the hyperimmune status of the selected plasma pool, since there was a six-fold increase in antibody level seen with the selected plasma pool. A similar relationship was found in a comparison of normal immune globulin (mean titer of 1:100,967) and VZV immune globulin (1:1,271,786). See Table 2.

TABLE 1

| Sample Identification | ELISA Titer |
|---|---|
| Unselected Plasma Pool No. 1 | 1:41,344 |

TABLE 1-continued

| Sample Identification | ELISA Titer |
| --- | --- |
| Unselected Plasma Pool No. 2 | 1:41,076 |
| Unselected Plasma Pool No. 3 | 1:45,201 |
| Unselected Plasma Pool No. 4 | 1:31,516 |
| Unselected Plasma Pool No. 5 | 1:26,996 |
| Unselected Plasma Pool No. 6 | 1:30,085 |
| Unselected Plasma Pool No. 7 | 1:21,801 |
| Unselected Plasma Pool No. 8 | 1:23,635 |
| Unselected Plasma Pool No. 9 | 1:22,131 |
| Unselected Plasma Pool No. 10 | 1:23,545 |
| Unselected Plasma Pool No. 11 | 1:21,700 | the geometric mean VZV antibody titer by ELISA of the 11 normal plasma pools is 1:28,833.

The fractionation method of Pappenhagen et al, U.S. Pat. No. 3,903,262 was followed. Briefly, Cohn Fraction II paste was prepared from the pooled plasma (400 liters) and was suspended in an aqueous sodium chloride solution, which was warmed and mixed with a solution of dithiothreitol. Iodoacetamide was added to the mixture. Next, the mixture was diafiltered to remove residual reagents. After pH adjustment, the material was sterile filtered.

The intravenously injectable VZV immune globulin produced from the "selected" plasma pool exhibited a titer of antibody to VZV of about 1:1,271,786 as measured by ELISA.

The titer of antibody to VZV of the selected plasma pool, of the high titer intravenously injectable VZV immune globulin produced from the selected plasma pool, and of 18 representative normal immune globulin lots produced from unselected plasma pools according to the fractionation method of Pappenhagen et al U.S. Pat. No. 3,903,262 is set forth in Table 2 below.

TABLE 2

| Sample Identification | Product Type | ELISA Titer |
| --- | --- | --- |
| Selected Plasma Pool | — | 1:173,346 |
| Hyperimmune Globulin | VZV-IGIV | 1:1,271,786 |
| Immune Globulin No. 1 | IGIV | 1:113,812 |
| Immune Globulin No. 2 | IGIV | 1:126,690 |
| Immune Globulin No. 3 | IGIV | 1:143,751 |
| Immune Globulin No. 4 | IGIV | 1:107,688 |
| Immune Globulin No. 5 | IGIV | 1:95,409 |
| Immune Globulin No. 6 | IGIV | 1:74,639 |
| Immune Globulin No. 7 | IGIV | 1:153,668 |
| Immune Globulin No. 8 | IGIV | 1:84,713 |
| Immune Globulin No. 9 | IGIV | 1:121,046 |
| Immune Globulin No. 10 | IGIV | 1:110,937 |
| Immune Globulin No. 11 | IGIV | 1:100,894 |
| Immune Globulin No. 12 | IGIV | 1:96,194 |
| Immune Globulin No. 13 | IGIV | 1:107,376 |
| Immune Globulin No. 14 | IGIV | 1:87,795 |
| Immune Globulin No. 15 | IGIV | 1:86,455 |
| Immune Globulin No. 16 | IGIV | 1:95,601 |
| Immune Globulin No. 17 | IGIV | 1:73,859 |
| Immune Globulin No. 18 | IGIV | 1:76,618 |

VZV-IGIV = varicella-zoster immune globulin, intravenously injectable, produced according to the method of this invention.
IGIV = immune globulin, intravenously injectable, produced from normal plasma.
The geometric mean ELISA Titer of the 18 IGIV lots is 1:100,967.

The data in Table 1 shows that the method according to the present invention affords a VZV immune globulin product having an antibody titer to VZV which approaches that disclosed in S. G. Paryani et al, *J. Pediatrics*, 105 (2), 200–205 (1984) for the VZIG product which is intended for intramuscular administration only. The VZV immune globulin product produced according to the present invention, by contrast, is intravenously administerable and possesses the above-described advantages.

EXAMPLE 2

The procedure described in Example 1 above may be followed except that the fractionation method of Tenold, U.S. Pat. Nos. 4,396,608 and 4,499,073 may be used in order to produce unmodified, or native, intravenously injectable VZV immune globulin.

Following this method, in the place of reducing and alkylating the globulin contained in the plasma according to Pappenhagen et al to render the product intravenously injectable, the pH and ionic strength of the solution of the globulin is adjusted so as to render the product intravenously injectable.

Although the antibody titer data of the starting plasma pool and the high titer intravenously injectable VZV immune globulin product produced according to the method of U.S. Pat. Nos. 4,396,608 and 4,499,073 are not available, it is expected that the antibody titers measured by ELISA will be substantially similar to those corresponding antibody titers described in Example 1 above.

What is claimed is:

1. An intravenously injectable immune globulin having a high titer of antibody to varicella-zoster virus in the range of from about 1:750,000 to about 1:1,500,000, as determined by an enzyme-linked immunosorbent assay, produced by
   (a) randomly screening plasma from donors who have not been vaccinated with a varicella-zoster virus vaccine for a titer of antibody to varicella-zoster virus of at least about 1:150,000, as determined by an enzyme-linked immunosorbent assay,
   (b) pooling the donor plasma selected according to step (a) above, thereby obtaining a six-fold increase in titer of antibody to varicella zoster virus in the plasma pool when compared with normal plasma pools,
   (c) preparing a immune globulin from the plasma pooled according to step (b) above, and
   (d) rendering the immune globulin obtained according to step (c) above intravenously injectable.

2. The intravenously injectable immune globulin of claim 1 wherein in step (d) the immune globulin is reduced and alkylated to render it intravenously injectable.

3. The intravenously injectable immune globulin of claim 1 wherein in step (d) the immune globulin is provided in solution and the pH and ionic strength of the solution is adjusted so as to render it intravenously injectable.

4. The pharmaceutical preparation of claim 1 comprising an amount of an intravenously injectable immune globulin effective to treat infection by varicella-zoster virus and a pharmaceutically acceptable carrier therefor.

5. The pharmaceutical preparation of claim 1 further including maltose.

6. The product of claim 1 wherein the immune globulin prepared in step (c) comprises at least 90% IgG monomer.

* * * * *